United States Patent [19]

Baba

[11] 4,011,015
[45] Mar. 8, 1977

[54] REFRACTOMETRIC DENSITOMETER

[75] Inventor: Nobuyuki Baba, Shin-nanyo, Japan

[73] Assignee: Toyo Soda Manufacturing Co., Ltd., Yamaguchi, Japan

[22] Filed: Sept. 29, 1975

[21] Appl. No.: 617,509

[30] Foreign Application Priority Data

Mar. 25, 1975 Japan .............................. 50-35806

[52] U.S. Cl. .............................. 356/136; 250/573
[51] Int. Cl.² ........................................ G01N 21/46
[58] Field of Search .......... 356/135, 136, 133, 134; 250/573, 248, 576

[56] References Cited

UNITED STATES PATENTS

| 2,050,486 | 8/1936 | Davis et al. | 356/136 |
| 2,780,131 | 2/1957 | Lanneau | 356/136 |

FOREIGN PATENTS OR APPLICATIONS

| 1,101,037 | 5/1965 | United Kingdom | 356/74 |

OTHER PUBLICATIONS

Wendlandt et al.; "Internal Reflection Spectroscopy"; Reflectance Spectroscopy, Interscience Publishers, 1966, p. 180.

Primary Examiner—Edward S. Bauer
Assistant Examiner—Conrad Clark
Attorney, Agent, or Firm—Oblon, Fisher, Spivak, McClelland & Maier

[57] ABSTRACT

A refractometric densitometer includes a first packing element and a first gasket disposed at one side of a glass element and a second packing element and a second gasket disposed at the other side of the glass element. A groove for passage of a reference material and a groove for passage of a sample are respectively formed in the first and second packing elements. An inlet pipe and an outlet pipe are formed in the first and second gaskets for passing the reference material or the sample to the grooves. The outlet pipe of the first gasket is connected to the inlet pipe of the second gasket. Multiple reflection is imparted to an incident light from the part of the glass element between the faced surfaces of the glass element contacting the first and second packing elements.

6 Claims, 5 Drawing Figures

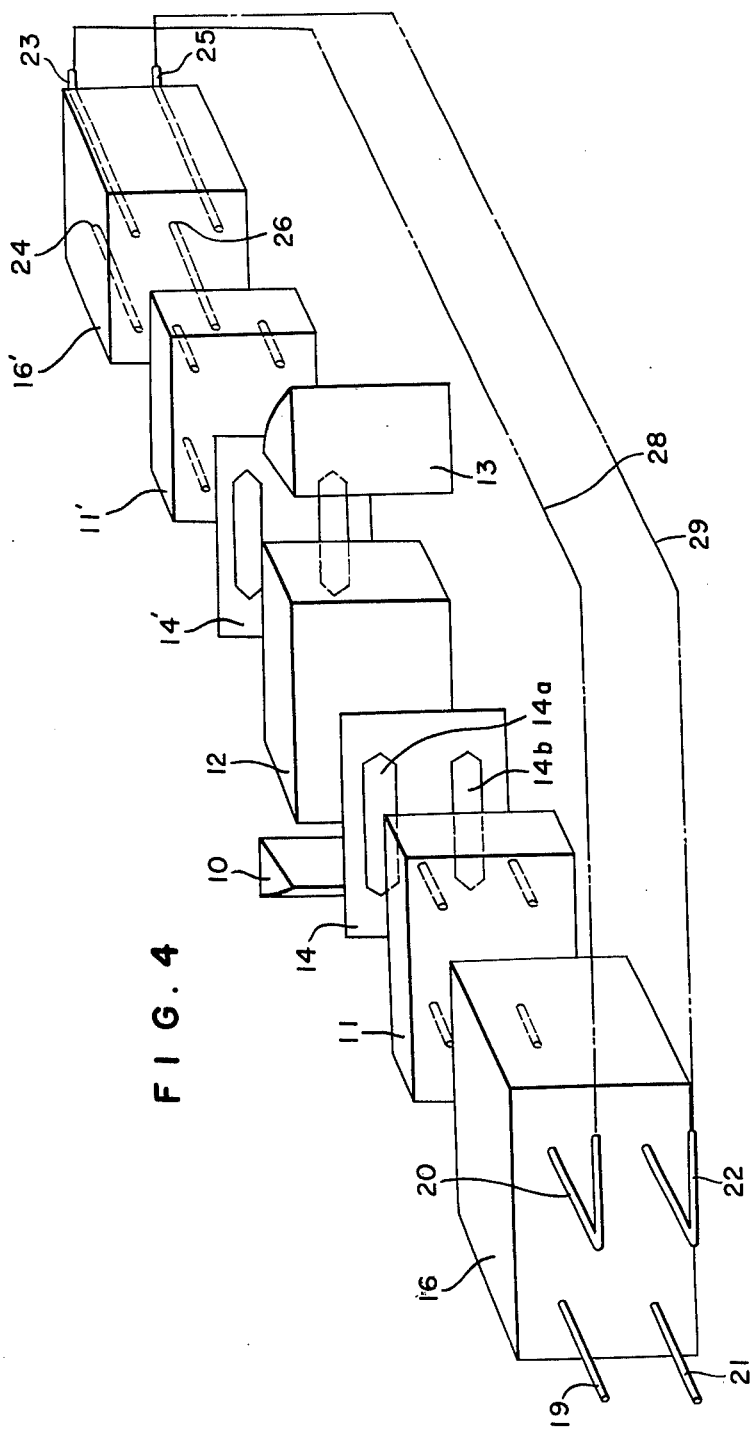

REFRACTOMETRIC DENSITOMETER

BACKGROUND OF THE INVENTION

1. Field of the Invention

The present invention relates to a refractometric densitometer which measures a low concentration of a solute contained in a solvent depending upon a difference between a refractive index of the solvent and that of the solution containing the solute. More particularly, it relates to a refractometric densitometer which measures the difference between the refractive index of the solvent and that of the solution containing the solute depending upon an optical principle concerning the Fresnel reflection of vibration of a reflected light quantity when the angle of incident light on the boundary surface between the solvent and the solution containing the solute is smaller than a critical angle.

2. Description of the Prior Art

In general, it is known to use a Brice type densitometer for measuring the declination of light based on the difference of the refractive index and a Fresnel reflection densitometer for detecting the variation of energy of the reflected light as a difference of the refractive index.

The former has a square shaped cell which is prepared by bonding plural glass plate with the result that it is difficult to prepare the cell with a small volume. Accordingly, the solute separated by chromatography is diffused in a cell having a relatively large volume with the result that the effectiveness of the chromatographic separation is less than desirable. Moreover, the cell is rather expensive and the transferred solution causes a turbulent flow in the cell with the result that the variation of the optical distance and the declination of the reflected light is detrimentally affected by the turbulent flow. Therefore, it has been difficult to provide a stable apparatus of high sensitivity.

Although the latter Fresnel type densitometer is in commercial use, with this apparatus, it is necessary to adjust the optical axis of the incident and reflected light because the refractive indices of the media for measurement are different. When a rectangular prism is used for the incident and the reflected light medium, a phenomenon of refraction of the incident light on the surface of the prism causes an incident point at the bottom of the prism to be shifted. Accordingly, it is difficult to effectively measure a wide range of refractive indices.

An apparatus using a cylindrical prism for the incident and the reflected light medium has been proposed to remedy this deficiency. However, this apparatus has the disadvantage that the reflected light is focused because of the lens effect causing an error when the reflected light quantity is measured by a light detector. Further the range of angles of incident and reflected light becomes wide with the result that the optical axial adjustment is difficult to attain yielding low reproducibility. With improved chromatographic separating technology, although the degree of separation can be increased and certain samples such as biochemical materials can be obtained in very small amounts, it is quite difficult to prepare a high concentration sample.

SUMMARY OF THE INVENTION

It is therefore an object of the present invention to provide a refractometric densitometer having high sensitivity and having a small volume cell.

It is another object of the present invention to provide a refractometric densitometer which can be utilized for precision measurement for a wide range of flow rates and which can be easily utilized for various samples with different refractive indices.

The foregoing and other objects are attained in accordance with one aspect of the present invention, through the provision of a refractometric densitometer comprising a first packing element and a first gasket disposed at one side of a glass element, a second packing element and a second gasket disposed at the other side of the glass element, a groove for passage of a reference material and a groove for passage of a sample respectively formed in the first and second packing elements, an inlet pipe and an outlet pipe formed in the first and second gaskets for passing the reference material or the sample to the grooves, means for connecting the outlet pipe of the first gasket to the inlet pipe of the second gasket, and means for imparting multiple reflection to an incident light from the part of the glass element between the faced surfaces of the glass element contacting the first and second packing elements.

BRIEF DESCRIPTION OF THE DRAWINGS

Various objects, features and attendant advantages of the present invention will be more fully appreciated as the same becomes better understood from the following detailed description when considered in connection with the accompanying drawings, in which:

FIG. 4 is a schematic assembly view of a part of the apparatus; and

DETAILED DESCRIPTION OF THE PREFERRED EMBODIMENT

Figure 1:
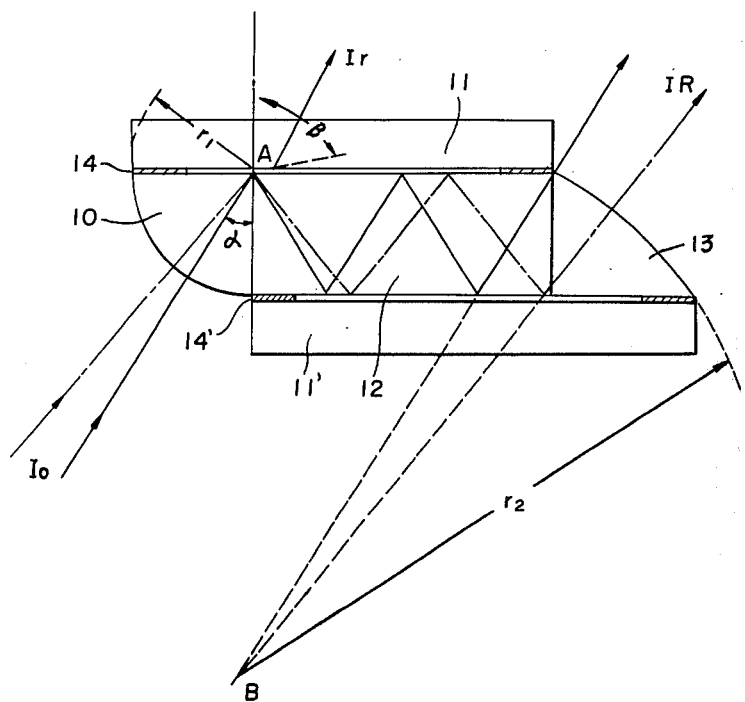
FIG. 1 illustrates the principle of operation of apparatus according to the invention.

The refractometric densitometer of the invention comprises a first packing element disposed at one side of a glass element, a first gasket, a second packing element disposed at the opposite side of the glass element, a second gasket, grooves formed on the first and second packing elements for passage of a reference solvent and passage of a sample, an inlet pipe and an outlet pipe formed in the first and second gaskets for passing the reference solvent and the sample to the grooves, means for connecting the outlet pipe of the first gasket and the inlet pipe of the second gasket and means for multiple-reflecting an indicent light from the glass element between a pair of faced surfaces of the glass element contacting the first and second packing elements.

The first and second packing elements can be made of synthetic resin, preferably polytetrafluoroethylene. The packing element can be varied depending upon whether there is a low flow rate of the sample solution or a high flow rate of the sample solution passed through the passage. The thickness of the packing elements is preferably in the range of 50 to 100μ.

In the densitometer of the invention, a reflection of the partial light passed from the first gasket element through the packing element on the surface of the gasket is prevented by inserting the second glass elements between the first packing element and the first gasket and between the second packing element and the second gasket. A semi-cylindrical prism for focusing the incident light to one side of the glass element is disposed to one side of the glass element and a prism formed by a curvature at a center of focus of an extended virtual reflected light is disposed at the other side of the glass element so that calibration for measurement of the incident and reflected light surface can be obtained.

Referring now to the drawings wherein like reference numerals designate identical or corresponding parts throughout the several views, the multiple reflection type Fresnel refractometric densitometer of the invention will be described.

The total reflection phenomenon occurs at a boundary surface when the angle of incidence is greater than a critical angle $\alpha c$ at which no refraction occurs at a boundary surface at which incident light passes from an optical medium of a high density to an optical medium of a low density.

The relation between reflective light intensity to incident light is given by the following equation using the Fresnel principle with the symbols shown in FIG. 1.

$$\frac{I_r}{I_o} = \frac{1}{2} \frac{\sin^2 (\beta - \alpha)}{\sin^2 (\beta + \alpha)} + \frac{1}{2} \frac{\tan^2 (\beta - \alpha)}{\tan^2 (\beta + \alpha)} \quad (1)$$

Figure 2:
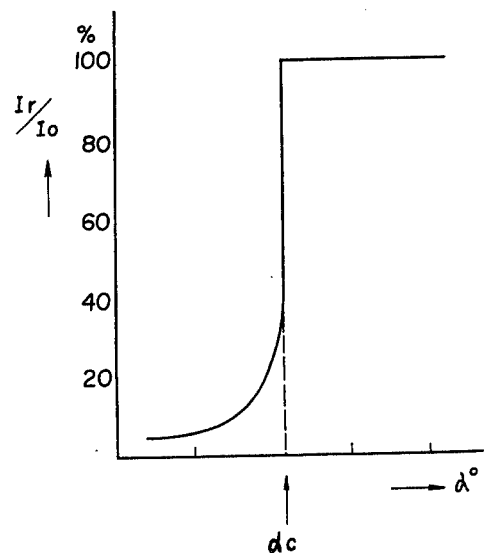
FIG. 2 is a graph showing incident angles to total reflected light.

The results are shown in FIG. 2.

When a solution containing a small amount of solute is in the cell, the variation $dR$ of the total reflected light $R$ to the variation of the refractive index $dn$ is expanded by application of Snell's law of the Fresnel principle to yield the following equation.

$$\frac{dR}{dn} = \frac{2}{n} \left[ \frac{\sqrt{1 - \left(\frac{\sin \alpha}{\sin \alpha c}\right)^2} - \frac{\cos \alpha}{\sin \alpha}}{\left\{\sqrt{1 - \left(\frac{\sin \alpha}{\sin \alpha c}\right)^2} + \frac{\cos \alpha}{\sin \alpha}\right\}^3} \right] \frac{\frac{\cos \alpha}{\sin \alpha c}}{\sqrt{1 - \frac{\sin \alpha}{\sin \alpha c}}} \quad (2)$$

wherein $n$ is a constant depending upon the refractive index of the solvent in the cell. The sensitivity $dR/dn$ is infinite when the incident angle $\alpha = \alpha c$. When the incident angle $\alpha$ of the abscissa is $\alpha c$ in FIG. 2, the reflected light intensity of the ordinate can be varied significantly.

The variation of the reflected intensity R to the variation of the refractive intensity caused by a slight change of concentration of the solute in the solvent is significantly changed by repeating the reflections. Accordingly, a quite small variation of the refractive index of the solution in the cell can be detected by measuring the multiple reflected light.

Figure 3:
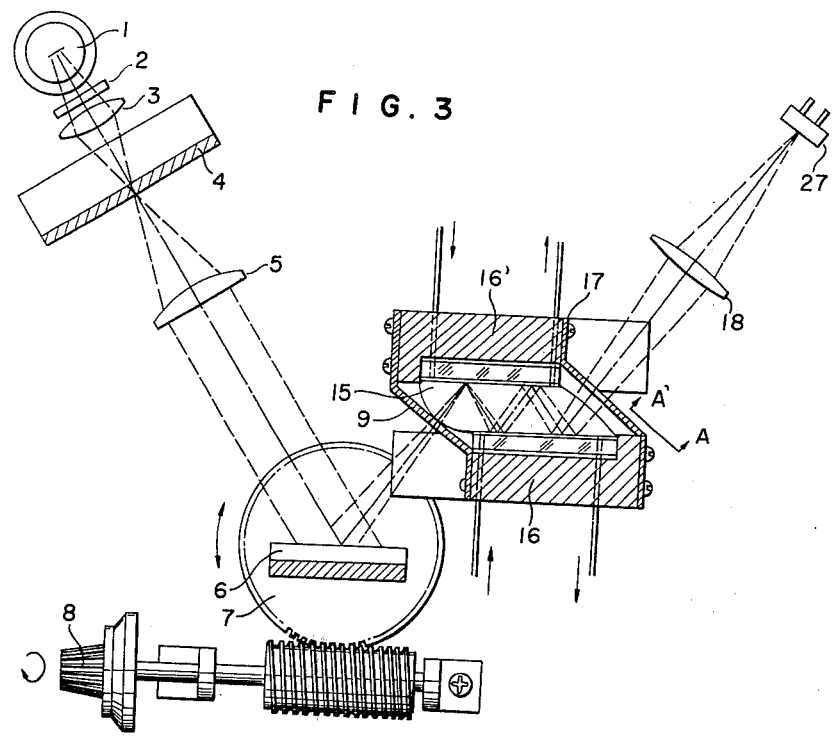
FIG. 3 is a schematic view of one embodiment of apparatus according to the invention.
Figure 5:
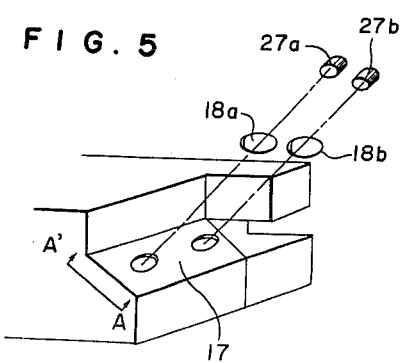
FIG. 5 is a schematic view of the part along line A - A' of FIG. 3.

FIG. 3 is a schematic view of one embodiment of the apparatus of the invention.

A light source 1 is a halogen lamp which has about five times the intensity of a tungsten lamp which is used in a conventional refractometric densitometer. Since an optical medium having a high refractive index such as a high flint glass or an optical crystal is used in the densitometer of the invention, the energy level of the reflected light is decreased two to three times as compared to use of a refractive index of 1.5. In order to compensate therefor, the halogen lamp is used.

The light from light source 1 becomes a monochromatic light after passage through a monochromatic filter 2 and is focussed by a lens 5 on a mirror 6 as parallel beams. The mirror 6 is disposed on a rotary disc 7 so as to vary the angle of the reflected light by turning a dial 8.

Usually, if the refractive index of a glass medium is constant and the angle of incident light is constant, the apparatus can be used only for the variation of concentration of a solute in a specific solvent.

It is necessary to measure concentrations of solutes in various solvents when the refractometric densitometer is used for liquid chromatography. Accordingly, the incident angle is adjusted depending upon the critical angle of each of the incident lights. Two pencils of light are taken from the parallel beams reflected by the mirror 6 by a mask 9 having two apertures at an inlet side and they are passed into the cell.

A prism 10 having a curvature $r_1$ from center point A is optically bonded on the side surface of the glass element 12 of the cell at an incident side and a prism 13 having a curvature $r_2$ from the center point B (a distance from a virtual focus of the reflected light passed from the other side of the glass element 12 to the upper side of the glass element) is optically bonded on the opposite surface of the glass element.

A pair of polytetrafluoroethylene packings 14, 14' having a thickness of 50~100μ and two grooves contact each of the upper and lower surfaces of the glass element 12. A pair of second glass elements 11, 11' are respectively disposed at the outer sides of the packing.

Since the thickness of the polytetrafluroethylene packings 14, 14' is small, the transmitting light $I_T$ is reflected on the surface of the gasket made of metal causing noise by passing into a light detector as a stray light component and adversely affecting the operation of the apparatus. Accordingly, each of the glass elements 11, 11' are inserted between each pair of packing and gasket i.e. between 14 and 16 and between 14' and 16' so as to discharge the transmitting light $I_T$.

A pair of gaskets 16, 16' made of anticorrosive metal such as stainless steel are respectively disposed on the outer surfaces of the glass elements 11, 11'. Each of the gaskets has two inlet passages and two outlet passages for the solution.

More particularly, the first gasket 16 has an inlet pipe 19 for the reference solvent and an inlet pipe 21 for the sample solution. These pipes are connected through the passages in the glass element 11 to the ends of the grooves 14a, 14b of the packing 14. The outlet pipe 20 for the reference solvent in the gasket 16 is connected through the pipe of the glass element to the outer end of the groove 14a of the packing 14. The outlet pipe for the sample solution is connected through the pipe of the glass element to the outer end of the groove 14b of the packing 14.

The second packing 14', the second glass element 11' and the second gasket 16' also have the same passages. However, the outlet pipe 20 for the reference solvent of the gasket 16 is connected through the joint pipe 28 shown by the dotted line in FIG. 4 to the inlet pipe 23 for the reference solvent of the gasket 16'. The outlet pipe 22 for the sample solution of the gasket 16 is connected to the inlet pipe 25 for the sample solution. Outlet pipes 24, 26 are connected. Accordingly, inlet pipes 19, 21 of the first gasket 16 are respectively passed through the grooves 14a, 14b of the first packing 14. Inlet pipes 23, 25 of the second gasket 16' are passed through the grooves 14'a 14'b of the second packing 14'.

The two parallel beam pencils separated by the mask 9 are respectively focused at the upper surface of the glass element 12 by passing through the semi-cylindrical prism having the curvature $r_1$. The two pencils of the reflected light are respectively multiple-reflected in the glass element 12 along the grooves for the reference solvent 14a, 14'a and the grooves for the sample solution 14b, 14'b. The repeatedly reflected lights are respectively calibrated by the prism 13 and are passed through the apertures of the mask at the outlet side and are focused by the lens 18a and the lens 18b. The two focused lights are passed to the transducing mechanism 27a, 27b of the photo detector 27 for conversion to electric signals.

A solvent having a constant refractive index is passed through the reference solvent passage. Accordingly, the multiple reflected light quantity is constant. When a solution containing a solute is passed through the sample solution passage, the variation of the concentration becomes a variation of the multiple reflected light quantity. Accordingly, the difference is generated by the electric circuit to yield the differential refractometric densitometer.

The apparatus of the invention has the above-mentioned structure. Accordingly, the apparatus can be used for various solvents having a wide range of refractive indices and adjustment can be easily made.

In the refractometric densitometer of the invention, the volume of the cell can be significantly reduced by forming the passage of the solution with the packing with a thickness of 50~100$\mu$ between the glass element and the gasket. It is also possible to change the flow rate of the sample solution in a wide range by using a packing having a different thickness. When the flow rate of the sample solution is high, the thickness of the packing should also be high.

The variation of the energy of the Fresnel reflected light can be increased by repeating the reflection on the boundary surface between the glass element and the solution so that a small variation of the refractive index of the solution in the cell can be detected with high sensitivity.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by letters patent of the United States is:

1. A refractometric densitometer comprising:
   a first packing element and a first gasket disposed at one side of a glass element,
   a second packing element and a second gasket disposed at the other side of the glass element,
   a groove for passage of a reference material and a groove for passage of a sample respectively formed in the first and second packing elements,
   an inlet pipe and an outlet pipe formed in the first and second gaskets for passing the reference material or the sample to the grooves,
   means for connecting the outlet pipe of the first gasket to the inlet pipe of the second gasket, and
   means for imparting multiple reflection to an incident light from the part of the glass element between the faced surfaces of the glass element contacting the first and second packing elements.

2. A refractometric densitometer according to claim 1, wherein second glass elements are respectively disposed between the first packing element and the first gasket and between the second packing element and the second gasket so that a reflection of a part of the light transmitted from the first glass element through the first packing element is prevented on the surface of the gasket.

3. A refractometric densitometer according to claim 1 wherein a semi-cylindrical prism for focusing the incident light to one end of the glass element is disposed at one side of the glass element, a prism formed by a curvature at a center of a focus on an extended virtual reflected light is disposed at the other side of the glass element to pass the multiple reflected light to a light detecting means so that calibration for measurement of the surface of the incident and reflected light is obtained.

4. A refractometric densitometer according to claim 1, wherein the thicknesses of the first and second packing elements are varied depending upon the flow rate.

5. A refractometric densitometer according to claim 4, wherein the thicknesses of the first and second packing elements are reduced for low flow rates.

6. A refractometric densitometer according to claim 4, wherein the thicknesses of the first and second packing elements are increased for high flow rates.

* * * * *